United States Patent

Anteunis et al.

[11] Patent Number: 5,770,692
[45] Date of Patent: Jun. 23, 1998

[54] CARBAMOYLATION OF AMINO GROUPS IN PEPTIDES VIA N-ARYLOXYCARBONYL INTERMEDIATES

[76] Inventors: Marc Anteunis, Welpengang, 12, B-9030 Mariakerke; Frank Becu, Gistelsteenweg, 440, B-8490 Jabbeke; Roland Callens, Varendrieskouter, 7, B-9031 Drongen; Georges Blondeel, Hoezestraat, 10, B-9300 Aalst, all of Belgium

[21] Appl. No.: 264,358

[22] Filed: Jun. 22, 1994

Related U.S. Application Data

[63] Continuation of Ser. No. 34,705, Mar. 19, 1993, abandoned.

[30] Foreign Application Priority Data

Mar. 20, 1992 [BE] Belgium ................................ 09200273

[51] Int. Cl.$^6$ .................................................. C07K 1/107
[52] U.S. Cl. .......................... 530/333; 530/335; 530/337; 530/345
[58] Field of Search ..................... 530/333, 337, 530/345

[56] References Cited

U.S. PATENT DOCUMENTS 3,928,305  12/1975  Werle .................... 260/112.5
4,725,645  2/1988  Anteunis et al. .................... 525/54.11
4,980,284  12/1990  Makryaleas .............................. 435/106
5,198,533  3/1993  Schally .................................... 530/313

FOREIGN PATENT DOCUMENTS 693604  8/1967  Belgium .
B0184243  2/1989  European Pat. Off. .......... C07K 1/00

OTHER PUBLICATIONS

Izdebski, *Synthesis* 423, 1989.
Madelmont *J Med Chem 28,* 1346 ('85).
Jaffé Chem Reviews 53, 191–261, 1953.
March, Adv Org Chem, 278–286, 1992.
Charton Chemtech 5, 245–255, 1975.
Charton Chemtech 4 502–511.
Lehninger, A.E., *Biochemistry,* 2nd edition, 1975, p. 149.
Boissonnas et al, *Helvetica Chimica Acta,* vol. 36, No. 4, 1953, pp. 875–886. [English summary on p. 886].
Houben–Weyl, *Methoden Der Organischen Chemie,* 4th Ed., vol. XV, No. 1, p. 472.

*Primary Examiner*—David Lukton

[57] ABSTRACT

Method of synthesising peptides containing one or more amino acid residues bearing an N-carbamoyl functional group, by aminolysis of N-aryloxycarbonyl derivatives, which are excellent synthesis intermediates for the preparation of various peptides containing amino acid residues bearing a ureino group, such as citrulline, homocitrulline, 2-amino-4-ureidobutyric residues.

14 Claims, No Drawings

CARBAMOYLATION OF AMINO GROUPS IN PEPTIDES VIA N-ARYLOXYCARBONYL INTERMEDIATES

This application is a Continuation of application Ser. No. 08/034,705, filed Mar. 19, 1993, now abandoned.

BACKGROUND OF THE INVENTION

The present invention relates to a new method of synthesising peptides containing one or more amino acid residues bearing an N-carbamoyl functional group. The invention also relates to new synthesis intermediates used in this method and to new peptide fragments.

Various synthetic peptides, used especially as reagents for analytical tests, as sweetening agents, as synthetic hormones or as medicinal products, contain amino acid residues bearing an N-carbamoyl functional group, either on the α-amino functional group of the N-terminal residue, or on the ω-amino functional group of a diamino acid residue, that is to say at the end of a side chain. Such diamino acids are especially norcitrulline (Nci), citrulline (Cit) or homocitrulline (Hci).

The introduction of an amino acid residue bearing an N-carbamoyl functional group into a peptide chain, starting directly with the amino acid carrying this carbamoyl functional group, has some disadvantages. Indeed, the presence of a ureido or ureino functional group seriously interferes with known methods of peptide synthesis, both in the "solid" phase based on the so-called Merrifield technique, and in the liquid phase. The chemical yields are poor and an adequate chiral purity is obtained only at the cost of laborious and costly purifications. Furthermore, in the case of diamino acids, the synthesis of amino acids bearing a ureido or ureino functional group at the end of the side chain, in pure enantiomorphous form, is difficult and therefore costly.

The synthesis of a peptide containing an amino acid residue bearing an N-carbamoyl functional group is therefore generally carried out in two stages. In a first step, a precursor peptide containing the amino acid residue bearing the amino functional group to be carbamoylated is synthesised. In a second step, the amino functional group to be carbamoylated is converted, inside the peptide chain, to a ureino functional group. For example, it is well known to convert, by carbamoylation by means of sodium isocyanate, the α-amino functional group of the N-terminal valine residue of the β chain of sickle cell hemoglobin, to a ureido functional group. (Lehninger A. L.; Biochemistry; (1975) second Edition, p. 149)

However, this known method does not appear to be satisfactory for peptide synthesis, mainly because of the insufficient specificity of the cyanates or isocyanates for the amino functional group(s) to be carbamoylated and because of the racemisation which may be induced by such a treatment.

Moreover, R. A. Boissonnas and G. Preitner (Helvetica Chimica Acta, (1953), Vol. 36 (4), p. 875–886) studied the removal of phenyloxycarbonyl (PhOC) and p-tolyloxycarbonyl (TOC) groups, which are used as groups for blocking the α-amino functional group of some α-amino acids, by means of various dissociating agents. All the dissociating agents used led to the complete removal of these groups and to the release of the α-amino functional group.

The invention overcomes the disadvantages of known methods of preparing N-carbamoyl-peptides by providing a new method for preparing N-carbamoyl-peptides with an improved chemical yield, which makes it possible to preserve to a remarkable extent the chiral purity of the structures used.

SUMMARY OF THE INVENTION

Consequently, the invention relates to a method of producing a peptide containing one or more N-carbamoyl functional groups, according to which an intermediate peptide containing one or more aryloxycarbonyl groups consisting of a group of general formula

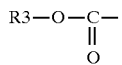

attached to the nitrogen atom of an amino functional group and in which R3 represents an aryl group, unsubstituted or substituted by one or more alkyl groups containing 1 to 4 carbon atoms, is reacted with a compound of general formula R1R2NH in which R1 and R2 represent, independently of each other, hydrogen atoms, alkyl, cycloalkyl or aralkyl radicals, containing at most 12 carbon atoms, or in which R1 and R2 together form an alicyclic radical containing 3 to 6 carbon atoms.

Peptide is understood to mean, for the purposes of the present invention, any natural or synthetic compound consisting of the combination of at least two natural or synthetic amino acids, and more particularly combined by an amide bond. In a wider sense, the term "peptide" is also understood to include any peptide structure some of whose functional groups are optionally substituted by protecting groups or activating groups.

Amino acid is understood to mean below any organic acid possessing at least one carboxyl functional group and at least one primary or secondary amino functional group, such as natural amino acids or synthetic amino acids. In a wider sense, the term "amino acid" is also understood to include below any amino acid some of whose functional groups are optionally substituted by protecting groups or activating groups. The amino acids are preferably those containing at least one carbon atom carrying both a carboxyl functional group and an amino functional group.

N-carbamoyl functional group is understood to mean below any carbamoyl functional group —CO—NH$_2$ attached to the nitrogen atom of an amino functional group of an amino acid or of a peptide. In a wider sense, the term "carbamoyl" is also understood to include below any carbamoyl functional group at least one of whose two hydrogen atoms is substituted by an alkyl, cycloalkyl or aralkyl radical containing at most 12 carbon atoms or whose two hydrogen atoms are substituted by a bivalent alicyclic radical containing 3 to 6 carbon atoms. The carbamoyl function group forms, with the nitrogen atom to which it is attached, a ureino or ureido functional group depending on whether the carbamoyl functional group is substituted or unsubstituted.

In the compound of general formula R1R2NH, alkyl, cycloalkyl, aralkyl or alicyclic radicals are understood to mean, for the purposes of the present invention, exclusively hydrocarbon radicals as well as hydrocarbon radicals substituted by functional groups comprising at least one oxygen, sulfur or nitrogen atom, such as carboxyl, hydroxyl, sulfhydryl, indolyl and imidazolyl groups.

In the remainder of the description, just as N-carbamoyl functional group is used to designate any carbamoyl functional group —CO—NH$_2$ attached to the nitrogen atom of an amino functional group of an amino acid or of a peptide, N-aryloxycarbonyl will be used to designate any aryloxycarbonyl group R3—O—CO— attached to the nitrogen atom of an amino functional group of an amino acid or of a peptide.

In the method according to the invention, the nature of R3 is critical. Indeed, it emerged, surprisingly, that unlike the conventional groups for protecting an amino functional group, such as for example the N-benzyloxycarbonyl group or the N-phthaloyl group, which groups, in the presence of ammonia or an amine, release the amino functional group unaltered, the N-aryloxycarbonyl groups lead, in the presence of such compounds, to the formation of an N-carbamoyl functional group. Generally, R3 is a group containing at most 12 carbon atoms. Most often, R3 is a phenyl, naphthyl, tolyl, xylyl, mesitylyl, ethylphenyl, diethylphenyl, propylphenyl or isopropylphenyl group. Preferably, R3 is a phenyl or tolyl group. In a particularly preferred manner, R3 is a phenyl or p-tolyl group. In this latter case, the intermediate peptide used in the method according to the invention is the N-phenyloxycarbonyl (PhOC) derivative or the N-tolyloxycarbonyl (TOC) derivative respectively. By analogy with the names PhOC and TOC, the various aryloxycarbonyl groups which can be used in the method according to the invention are designated below by the generic abbreviation ArOC.

Excellent results have been obtained in the method according to the invention with R1R2NH compounds for which R1 and R2 radicals are hydrogen atoms or exclusively hydrocarbon radicals. Such compounds are, for example, ammonia or the primary or secondary amines chosen from alkylamines, cycloalkylamines, aralkylamines and heterocyclic amines. These amines generally contain at most 12 carbon atoms. By way of nonlimitative examples, there may be mentioned, as alkylamines, methylamine, ethylamine, n-propylamine, isopropylamine, n-butylamine, tert-butylamine, 2-methylbutylamine, dimethylamine, diethylamine and N-methyl-N-ethylamine, as cycloalkylamines, cyclopentylamine and cyclohexylamine, as aralkylamines, benzylamine, N-(phenylethyl)amine, N-(phenylpropyl) amine and N-(phenylbutyl)amine, as heterocyclic amines, pyrrolidine and piperidine.

By way of illustration of R1R2NH compounds for which R1 and/or R2 radicals are hydrocarbon radicals substituted by functional groups comprising at least one oxygen, sulfur or nitrogen atom, there may be mentioned the amino acids, as defined above.

In the case where the compound R1R2NH is ammonia, the N-carbamoyl functional group formed by the method according to the invention is unsubstituted and the peptide obtained therefore contains a ureido functional group. In all the other cases (R1 and/or R2 different from H), the N-carbamoyl functional group formed by the method according to the invention is substituted by at least one group containing one or more carbon atoms and the peptide obtained thus contains a ureino functional group.

In a peptide, 2 types of amino functional groups are capable of being carbamoylated: on the one hand, the α-amino functional group of the N-terminal residue and, on the other hand, the ω-amino functional group of a diamino acid residue regardless of the position of this diamino acid within the peptide chain.

The method according to the invention makes it possible to prepare $N^\omega$-carbamoyl-peptides and $N^\alpha$-carbamoyl-peptides. $N^\alpha$-carbamoyl-peptide is understood to mean any peptide bearing a carbamoyl functional group, as defined above, on the α-amino functional group of the N-terminal residue of a peptide chain. $N^\omega$-carbamoyl-peptide is understood to mean any peptide bearing a carbamoyl functional group, as defined above, on one or more ω-amino functional groups of any diamino acid residue situated in any position in the peptide chain.

The method according to the invention appears to be particularly efficient for the production of $N^\omega$-carbamoyl-peptides starting with an intermediate peptide bearing an aryloxycarbonyl group on one or more ω-amino functional groups. Preferably, the method according to the invention is used for converting, inside a peptide structure, a lysine, ornithine or 2,4-diamino-butyric residue, whose ω-amino functional group at the end of a side chain is substituted by an ArOC group, to a homocitrulline, citrulline or 2-amino-4-ureido-butyric (norcitrulline) residue respectively, regardless of their configuration (D, L or DL).

The intermediate peptide, containing one or more N-aryloxycarbonyl groups, which is used in the method according to the invention may additionally contain other functional groups substituted by protecting groups or activating groups.

Protecting group or activating group are understood to mean any compound cited in the literature for this purpose. By way of illustration of such protecting or activating groups capable of substituting one or more functional groups of the intermediate peptide containing one or more N-aryloxycarbonyl groups used in the method according to the invention, there may be mentioned:

a) as groups protecting the amino functional group,
   substituted or unsubstituted groups of the alkyl or aralkyl type, containing heteroatoms or otherwise, such as benzyl, diphenylmethyl, di(methoxyphenyl) methyl and triphenylmethyl (trityl) groups,
   substituted or unsubstituted groups of the acyl type such as especially formyl, acetyl, trifluoroacetyl, benzoyl and phthaloyl groups,
   substituted or unsubstituted groups of the aralkyloxycarbonyl type such as especially benzyloxycarbonyl, p-chlorobenzyloxycarbonyl, p-bromobenzyloxycarbonyl, p-nitrobenzyloxycarbonyl, p-methoxybenzyloxycarbonyl, benzhydryloxycarbonyl, 2-(p-biphenylyl) isopropyloxycarbonyl, 2-(3,5-dimethoxyphenyl) isopropyloxycarbonyl, p-phenylazobenzyloxycarbonyl), triphenylphosphonoethyloxycarbonyl and 9-fluorenylmethyloxycarbonyl groups,
   substituted or unsubstituted groups of the alkyloxycarbonyl type such as especially tert-butyloxycarbonyl, tert-amyloxycarbonyl, diisopropylmethyloxycarbonyl, isopropyloxycarbonyl, ethyloxycarbonyl, allyloxycarbonyl, 2-methylsulphonylethyloxycarbonyl and 2,2,2-trichloroethyloxycarbonyl groups,
   groups of the cycloalkyloxycarbonyl type such as especially cyclopentyloxycarbonyl, cyclohexyloxycarbonyl, adamantyloxycarbonyl and isobornyloxycarbonyl groups,
   groups derived from heteroatoms, such as benzenesulphonyl, p-toluenesulphonyl (tosyl), mesitylenesulphonyl, methoxytrimethylphenylsulphonyl, o-nitrophenylsulphenyl and trimethylsilyl groups,
b) as groups protecting the carboxyl functional group, groups such as especially methyl, ethyl, t-butyl, cyclohexyl, benzyl, p-nitrobenzyl, phenacyl, trimethylsilyl, carboxamidomethyl and fluorenylmethyl groups, c) as groups protecting the hydroxyl functional group, groups such as especially t-butyl, tetrahydropyranyl, benzyl, trimethylsilyl, methoxymethyl, trityl and fluorenylmethyl groups, d) as activating groups especially O-succinimidoyl, O-norbornenedicarboximidoyl, O-benzotriazolyl, O-oxodihydrobenzotriazolyl, O-hydroxypyridyl, pentachlorophenyl, trichlorophenyl, pentafluorophenyl, isobutyloxycarbonyl and trimethylacetyl groups.

In a first embodiment of the method for producing an N-carbamoyl-peptide according to the invention, the intermediate peptide containing one or more N-ArOC groups is synthesised starting with the N-ArOC derivative of an amino acid, that is to say by incorporation into the peptide chain of the amino acid of which it is desired to convert an amino functional group to a ureido or ureino functional group, directly in the form of its N-ArOC derivative. Indeed, it emerged, surprisingly, that these N-ArOC derivatives of amino acids are not only remarkably stable, but are furthermore excellent at preserving the chirality of the compounds, which allows their use in conventional chemical methods for peptide synthesis both in the solid phase and in the liquid phase. The use, as reagent for synthesising the intermediate peptide, of the amino acid which is N-substituted in the ArOC group is particularly advantageous. Indeed, the ArOC group acting, in a remarkably effective manner, as the group protecting the amino functional group in question, and also as an intermediate, particularly one which is specific for the desired ureido or ureino functional group while preserving the chirality of the compounds, this embodiment of the method according to the invention makes it possible to prepare the desired N-carbamoyl-peptide with a yield never achieved before.

The N-ArOC derivative of the amino acid, for which it is desired to produce in fine the N-carbamoyl derivative inside a peptide, may be conventionally prepared by a method similar to those used for attaching onto an amino functional group a protecting group of the alkyloxycarbonyl or aralkyloxycarbonyl type. A conventional method, known as the Schotten-Baumann procedure, consists in reacting, in an aqueous medium, the sodium form of the amino acid with the desired aryl chloroformate. Another procedure which gives excellent results and which is therefore preferred, consists in using the amino acid in the form of its persilylated derivative. This persilylated derivative may be produced for example by a treatment under reflux with an excess amount of trimethylcyanosilane until a homogeneous solution is produced. This solution is then diluted, for example with methylene chloride, and cooled to a temperature of less than −10° C., preferably less than or equal to −15° C. The stoichiometric quantity of aryl chloroformate is then added very slowly, then after reacting for a few minutes, the solution is concentrated and the N-ArOC-amino acid is isolated via the most appropriate route, depending on its physicochemical properties.

This first embodiment of the method according to the invention is preferred when it is desired to incorporate in fine, inside a peptide, the $N^\omega$-carbamoyl derivative of a diamino acid. In this special case of (α,ω-diamino acids, where it is necessary selectively to block the amino functional group of the side chain, the $N^\omega$-ArOC derivative may be prepared by using the well known techniques of selective acylation, for example by means of the copper(II) complex according to a procedure similar to that described especially in "Methoden Der Organischen Chemie" (HOUBEN-WEYL), 1974, Volume XV/1, p. 472, with respect to $N^\epsilon$-benzyloxycarbonyl-L-lysine.

In this specific case of α,ω-diamino acids, depending on the method of peptide synthesis and depending on the strategy used, the $\alpha$-$NH_2$ functional group may be blocked, if necessary, by any customary protecting group or may constitute the amine-containing component to be introduced into a peptide chain whose carboxyl terminal functional group is activated in a conventional manner. The $N^\omega$-ArOC-amino acid may be coupled to this chain, for example in silylated form, it being possible to carry out the silylation by means especially of trimethylsilyl chloride and triethylamine, hexamethyldisilazane, bistrimethylsilylacetamide, or trimethylcyanosilane (TMSCN), as described in European Patent EP-B-184243. Any other coupling method may also be used such as, for example, the use of the $N^\omega$-ArOC-amino acid as it is, in combination with an active ester, in a semi-aqueous medium.

Similarly, depending on the method of peptide synthesis and depending on the strategy used, the carboxyl functional group of any N-ArOC-amino acid may be optionally blocked by a customary protecting group or activated by a conventional activating agent.

After incorporation of the N-ArOC-amino acid into a peptide fragment, the peptide synthesis may be continued in a conventional manner by condensation between a fragment reacting via its amino functional group (amine-containing component) and a fragment reacting via its carboxyl functional group (carboxylic component). The presence of the N-ArOC group, both on the amine-containing component and on the carboxylic component does not in any way interfere either with the coupling with other amino acids or peptide fragments, or with the methods of activation normally used.

This first embodiment of the method according to the invention is particularly preferred for synthesising peptides containing L, D, DL 2-amino-4-ureido-butyric (norcitrulline), citrulline and homocitrulline residues from the corresponding L, D or DL precursor amino acids respectively, that is to say from 2,4-diaminobutyric acid, ornithine and lysine respectively. These amino acids may be introduced without difficulty into an intermediate peptide chain, preferably directly in the form of their $N^\omega$-PhOC or $N^\omega$-Toc derivatives, which derivatives are subsequently converted in situ inside the peptide or a peptide fragment to an $N^\omega$-carbamoyl derivative with a very high yield and, in the case of the D or L structures, without modification of the chiral purity, which is a key element in physiological or therapeutic activity.

In a second embodiment of the method for producing N-carbamoyl-peptides according to the invention, the intermediate peptide containing one or more N-ArOC groups is synthesised starting with a precursor peptide, by introducing the ArOC group onto the amino functional group(s) to be carbamoylated inside the peptide chain and not in the amino acid. This embodiment of the method may be used especially to carbamoylate one or more free amino functional groups of a natural peptide, but may also be used in the case of synthetic peptides. In this latter case, the intermediate peptide is prepared in two successive stages: a first stage consists in the synthesis of the precursor peptide containing the amino acid residue bearing the amino functional group to be carbamoylated, starting with the various amino acids forming it, and a second stage consisting in the conversion of the precursor peptide to an intermediate peptide containing an N-ArOC group. The amino acid of which it is desired to convert an amino functional group to a ureido or ureino functional group is incorporated into the peptide chain of the precursor peptide in a conventional manner, masking this amino functional group during the peptide synthesis by a customary protecting group, for example by a benzyloxycarbonyl, tert-butyloxycarbonyl or phthaloyl group. At a subsequent stage of the synthesis, after incorporation into the peptide chain of the amino acid residue containing the protected amino functional group and at the most appropriate time depending on the strategy adopted, the customary group protecting this functional group is removed in the conventional manner so as to obtain the precursor peptide.

In the natural or synthetic precursor peptide, the amino functional group which it is desired to carbamoylate, at that time in the free form, is then converted, in a second stage, to an ArOC-amino functional group to form the intermediate peptide. The introduction of this ArOC group is carried out by reaction of this free amino functional group with an aryloxycarbonylating agent, for example with an aryl chloroformate or with an aryloxycarbonyloxysuccinimide. In the case where the amino functional group to be carbamoylated is a ω-amino functional group, the introduction of the ArOC group may be conventionally carried out by a method similar to those used for attaching onto an amino functional group a conventional protecting group, such as the benzyloxycarbonyl group. In the case where the amino functional group to be carbamoylated is a α-amino functional group, one procedure for introducing the N-ArOC group which gives excellent results and which is therefore preferred, consists in using the precursor peptide in the form of its persilylated derivative, which derivative may be obtained in a manner known per se, by reaction with a silylating agent considered above. The persilylated derivative is placed in contact with the aryloxycarbonylating agent, preferably in stoichiometric proportions, in a water-immiscible solvent. Suitable solvents are especially methyl tert-butyl ether, dichloromethane and ethyl acetate. This latter solvent is preferred. The reaction between the persilylated derivative and the aryloxycarbonylating agent is carried out at a temperature of 0° to 40° C., preferably at room temperature. After reacting for a few minutes, preferably not more than two minutes, water is added to the reaction medium and the two-phase system obtained is stirred for a period of about 10 to 30 minutes. After separating the phases, the intermediate peptide containing the N-ArOC group is then isolated from the organic phase by the most appropriate route, according to its physicochemical properties. This preferred procedure makes it possible to prepare the intermediate peptide in a very selective manner, while preserving the chirality of the compounds and avoiding the formation of by-products of a heterocyclic nature.

Preferably, after purification of the intermediate peptide containing the N-ArOC group(s) by any known method, for example by crystallisation, the said peptide is placed in contact with a compound R1R2NH as defined above, to give, by the method according to the invention, the peptide in which the free amino functional group of the precursor peptide has been converted to a ureino functional group.

Using a conventional group for protecting the amino functional group to be carbamoylated in order to introduce this amino acid into the peptide chain of the precursor peptide, which protecting group must subsequently be removed and replaced by an ArOC group to give the intermediate peptide, this second embodiment of the method according to the invention involves, for a synthetic peptide, a greater number of steps than the first embodiment of the method in which the intermediate N-ArOC-peptide is prepared from the outset with an N-ArOC amino acid. Consequently, when the peptide to be carbamoylated is a peptide prepared by the synthetic route starting with the constituent amino acids, the first embodiment of the method for producing N-carbamoyl-peptides according to the invention is preferred. On the other hand, in the case of natural peptides, the second embodiment of the method for producing N-carbamoyl-peptides according to the invention is preferred.

Regardless of the method for incorporating the N-ArOC group into the peptide structure, the amino acid residue bearing an N-ArOC group is then converted in situ, inside the peptide chain, at a time judged most appropriate, by reaction with a compound R1R2NH as defined above, to give, by the method according to the invention, the corresponding N-carbamoyl-peptide.

The compound R1R2NH is used in excess relative to the intermediate N-ArOC-peptide, generally in a quantity 2 times greater than the stoichiometric quantity, the most often in a quantity 5 to 100 times, preferably 5 to 20 times, greater than the stoichiometric quantity. The reaction is carried out in any appropriate medium, especially in an organic solvent such as tetrahydrofuran, dimethylformamide, ethyl acetate or an alcohol such as methanol. The compound R1R2NH is used either in anhydrous form, or in concentrated aqueous solution. The reaction is generally carried out at a temperature of −20° to +50° C. Preferably, the method according to the invention is carried out at a temperature of 0° to 20° C., such a temperature making it possible to obtain a good reaction rate while preserving a very high selectivity.

It is evident that the other protecting groups which may be present in the intermediate peptide structure during the use of the method according to the invention must be stable under the conditions of ammonolysis or of aminolysis of the N-ArOC group, unless it is desired to take advantage of the ammonolysis or the aminolysis of the method according to the invention to remove at the same time the other protecting groups still present in the peptide structure.

The invention also relates to the diamino acids N^ω-substituted by an ArOC group and the intermediate peptides containing one or more diamino acid residues N^ω-substituted by an ArOC group. These diamino acids and intermediate peptides may be optionally substituted, protected or activated. Consequently, the invention relates to the compounds corresponding to the general formula

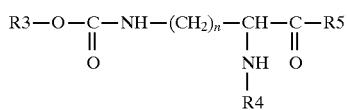

in which

R3 represents an aryl group which is unsubstituted or substituted by one or more alkyl groups containing 1 to 4 carbon atoms R4 represents a hydrogen atom, a group for protecting the amino functional group, an amino acid or a peptide some of whose functional groups are optionally substituted by a protecting group or by an activating group R5 represents a hydroxyl group, a halogen atom, a group for protecting the carboxyl functional group, an activating group, an amino group, an amino acid or a peptide some of whose functional groups are optionally substituted by a protecting group or by an activating group n is an integer from 1 to 10.

As nonlimitative examples of groups for protecting the amino functional group which may be represented by R4, there may be mentioned especially substituted or unsubstituted groups of the alkyl or aralkyl type, such as benzyl, diphenylmethyl, di(methoxyphenyl)methyl and triphenylmethyl (trityl) groups, substituted or unsubstituted groups of the acyl type such as formyl, acetyl, trifluoroacetyl, benzoyl and phthaloyl groups, substituted or unsubstituted groups of the aralkyloxycarbonyl type such as benzyloxycarbonyl, p-chlorobenzyloxycarbonyl, p-bromobenzyloxycarbonyl, p-nitrobenzyloxycarbonyl, p-methoxybenzyloxycarbonyl, benzhydryloxycarbonyl, 2-(p-biphenylyl)isopropyloxycarbonyl, 2-(3,5-dimethoxyphenyl)isopropyloxycarbonyl, p-phenylazobenzyloxycarbonyl), triphenylphosphonoethyloxycarbonyl and 9-fluorenylmethyloxycarbonyl groups, substituted or unsubstituted groups of the alkyloxycarbonyl type such as tert-butyloxycarbonyl, tert-amyloxycarbonyl, diisopropylmethyloxycarbonyl, isopropyloxycarbonyl, ethyloxycarbonyl, allyloxycarbonyl, 2-methylsulphonylethyloxycarbonyl and 2,2,2-trichloroethyloxycarbonyl groups, groups of the cycloalkyloxycarbonyl type such as cyclopentyloxycarbonyl, cyclohexyloxycarbonyl, adamantyloxycarbonyl and isobornyloxycarbonyl groups, groups containing a heteroatom, such as benzenesulphonyl, p-toluenesulphonyl (tosyl), mesitylenesulphonyl, methoxytrimethylphenylsulphonyl, o-nitrophenylsulphenyl and trimethylsilane groups.

As nonlimitative examples of groups for protecting the carboxyl functional group which may be represented by R5, there may be mentioned especially methyl, ethyl, t-butyl, cyclohexyl, benzyl, p-nitrobenzyl, phenacyl, trimethylsilyl, carboamidomethyl and fluorenylmethyl groups.

As nonlimitative examples of activating groups which may be represented by R5, there may be mentioned especially O-succinimidoyl, O-norbornenedicarboximidoyl, O-benzotriazolyl, O-oxodihydrobenzotriazolyl, O-hydroxypyridyl, pentachlorophenyl, trichlorophenyl, pentafluorophenyl, isobutyloxycarbonyl and trimethylacetyl groups.

Generally, R3 is a group containing at most 12 carbon atoms. Most often, R3 is a phenyl, naphthyl, tolyl, xylyl, mesitylyl, ethylphenyl, diethylphenyl, propylphenyl or isopropylphenyl group. Preferably, R3 is a phenyl or tolyl group. In a particularly preferred manner, R3 is a phenyl or p-tolyl group.

Preferably, n is an integer from 2 to 6. In a particularly preferred manner, n is an integer from 2 to 4.

Finally, compounds which give very good results in the method according to the invention are especially those where:
R3 represents a phenyl group
R4 represents a hydrogen atom or the dipeptide Z-Ser-Tyr-
R5 represents a hydroxyl group, an amino acid or a peptide some of whose functional groups are optionally substituted by a protecting group or by an activating group
n is equal to 2, 3 or 4.

These preferred compounds according to the invention are N$^\omega$-PhOC derivatives of 2,4-diaminobutyric acid, ornithine or lysine and peptides or peptide structures containing an N$^\omega$-PhOC derivative of a residue of one of these diamino acids, regardless of their configuration (D, L or DL).

As examples, there may be mentioned, as compounds according to the invention, N$^\gamma$-PhOC-diaminobutyric acid and the peptides containing a diaminobutyric residue in any position, whose γ-amino functional group is substituted by a PhOC group; N$^\delta$-PhOC-D-ornithine and the peptides containing a D-ornithine residue in any position, whose δ-amino functional group is substituted by a PhOC group; N$^\epsilon$-PhOC-lysine and the peptides containing a lysine residue in any position, whose ε-amino functional group is substituted by a PhOC group. A peptide containing a diamino acid residue N$^\omega$-substituted by an ArOC group is for example the tripeptide Z-Ser-Tyr-D-Orn(PhOC).

These compounds according to the invention are excellent synthesis intermediates for the preparation of various peptides including amino acid residues bearing a ureino group, such as the citrulline, homocitrulline, 2-amino-4-ureidobutyric residues: the N$^\omega$-ArOC amino acids may be easily incorporated into intermediate peptide structures, which structures may then be easily converted to N$^\omega$-carbamoyl-peptides by the method according to the invention.

In particular, these compounds are excellent intermediates for the manufacture, in liquid phase, of fragments of modified hormones.

The invention also relates to the peptides of general formula

in which
R6 is a hydrogen atom or a group for protecting the amino functional group,
Ser(R7) is a serine residue with R7 representing a hydrogen atom or a group for protecting the hydroxyl functional group of the side chain of the serine residue
Tyr(R8) is a tyrosine residue with R8 representing a hydrogen atom or a group for protecting the hydroxyl functional group of the side chain of the tyrosine residue
R9 is, in a first variant, a 2,4-diaminobutyric or ornithine residue of the D, L or DL configuration, and in a second variant, a 2-amino-4-ureidobutyric, citrulline or homocitrulline residue of the D, L or DL configuration, in which the hydrogen atoms of the carbamoyl functional group are optionally substituted by an alkyl, cycloalkyl or aralkyl group containing at most 12 carbon atoms, or by a cycloalkylene group containing 3 to 6 carbon atoms.
R10 is a hydroxyl radical, an amino acid or a peptide some of whose functional groups are optionally substituted by a protecting group.

As nonlimitative examples of groups for protecting the amino functional group, which may be represented by R6, there may be mentioned especially benzyloxycarbonyl and tert-butyloxycarbonyl groups.

As nonlimitative examples of groups for protecting the hydroxyl functional group of the side chain of the serine residue or the tyrosine residue, which may be represented by R7 or by R8, there may be mentioned especially benzyl, benzyloxycarbonyl, trimethylsilyl groups.

Preferably, R9 represents residues with a D configuration. Preferably, R10 is a hydroxyl radical or a peptide fragment containing 1 to 5 amino acids. In a particularly preferred manner, R10 is a hydroxyl radical.

When R9 is an amino acid residue according to the first variant, the peptides are especially precursors of some intermediate peptides containing an N-aryloxycarbonyl group used in the method according to the invention. The preparation of these precursor peptides may be carried out by any conventional method of peptide synthesis, either in "solid" phase according to the technique described by Merrifield, or in liquid phase.

When R9 is an amino acid residue according to the second variant, the peptides are especially fragments of some modified hormones. The preparation of these peptide fragments may be easily carried out in liquid phase by means of the method according to the invention, by using their $N^\omega$-ArOC intermediates according to the invention, optionally obtained starting with the precursor peptides above.

The symbolic representations of the amino acids and peptides adopted in the description and the examples follow the IUPAC recommendations on nomenclature, which are generally adopted and described for example in "Nomenclature and Symbolism for Amino Acids and Peptides, Recommendations 1983", Eur. J. Biochem. (1984), 138, p. 9–37. By convention, the peptides are represented with their N-terminal end to the left and their C-terminal end to the right. The abbreviations used to designate the amino acid residues are derived from the trivial names of the amino acids and are $A_2$bu, 2,4-diaminobutyric acid; Orn, ornithine; Lys, lysine; Nci, 2-amino-4-ureidobutyric acid or norcitrulline; Cit, citrulline; Hci, homocitrulline; Ser, serine; Tyr, tyrosine; Leu, leucine; Arg, arginine; Pro, proline; Gly, glycine; Ala, alanine. Unless otherwise stated, all the amino acids described are amino acids of the L form.

The various products and synthesis intermediates reported in the examples were characterised by various analytical methods which are used under the following conditions:

thin-layer chromatography (TLC):
silica gel plates MERCK 60F-254
eluents:
Rf(1) HCOOMe:HCOOH:MeOH 95:2.5:2.5
Rf(2) EtOAc:EtOH:HOAc 8:1:1
Rf (3) $CH_3CN$:$CHCl_3$:HOAc;$H_2O$ 7:7:4:2
Rf(4) HCOOMe;HCOOH:MeOH:$H_2O$ 92.5:2.5:2.5:2.5

HPLC chromatography:
column: Vydac $5\mu$ C18
elution: gradient from 98% A+2% B up to 25% A+75% B in 49 minutes (A=$H_2O$ containing 0.1% TFA; B=$CH_3CN$ containing 0.1% TFA) .
flow rate=2 ml/min
detection: UV 220 nm.

nuclear magnetic resonance (NMR):
apparatus: Brüker AMX 500 MHz
shift given in ppm
course of the resonances: m=multiplet, s=singlet, d=doublet, t=triplet, q=quadruplet, quint=quintuplet.

The following abbreviations are used in the examples below:
α=optical rotation, measured at 589 nm at 25° C.
$CH_3CN$=acetonitrile
DMF=dimethylformamide
EtOAc=ethyl acetate
EtOH=ethyl alcohol
HCOOH=formic acid
HCOOMe=methyl formate
HOAc=acetic acid
i.BuOCOCl=isobutyl chloroformate
MeOH=methyl alcohol
MTBE=methyl tert-butyl ether
NMM=N-methylmorpholine
NMP=N-methylpyrrolidone
PhEt=phenylethyl
PhOC=phenyloxycarbonyl
PhOC-OSu=phenyloxycarbonyloxysuccinimide
Pht=phthaloyl
PivCl=pivaloyl chloride
m.p.=melting point
Pyr=pyridine
TEA=triethylamine
TFA=trifluoroacetic acid
THF=tetrahydrofuran
TMS=trimethylsilyl
TMSCN=trimethylcyanosilane
Z=benzyloxycarbonyl

DESCRIPTION OF THE PREFERRED EMBODIMENTS

EXAMPLE 1

Preparation of $N^\epsilon$-PhOC-lysine from lysine

A solution containing 36.5 g of LysHCl and 16 g of NaOH in 200 ml of water is mixed with 25 g of $CuSO_4.5H_2O$ dissolved in 80 ml of water. 25 g of $NaHCO_3$ are then introduced, with stirring.

After dissolution of the bicarbonate, the solution is cooled to 0° C. and then treated dropwise with 30 ml of phenyl chloroformate (duration of the introduction 1 h). After allowing to stand for 3 h at room temperature, the precipitate formed is filtered, washed twice with 200 ml of water, twice with 200 ml of acetone and then air dried. The copper(II) complex thus obtained is suspended in 400 ml of water and then decomposed by the addition of 80 ml of concentrated HCl. The copper(II) ions are then precipitated by the addition, in small portions, of the stoichiometric quantity of sodium sulphide. After degassing in order to remove the $H_2S$ which may have formed, the suspension is mixed with 10 g of celite.

After filtration and washing of the cake with 200 ml of water, the pH of the filtrate is adjusted to 7 by introduction of $NaHCO_3$. $N^\epsilon$-PhOC-Lys precipitates. After 1 h at 0° C., it is collected by filtration, washed with water, with methanol and with acetone and then dried. Yield: 45 g (84%)

m.p.: 211°–215° C. (decomp.
α:+16.6 (c=1/1N HCl)
TLC: Rf (3)=0.50
HPLC: $t_R$=11.70 min
NMR ($^1$H): (ref. DMSO-$d_6$ at 2.49 ppm; product dissolved in DMSO-$d_6$ by adding a drop of TFA)
8.27 (3H broad s) NH3 7.70 (1H broad s) NH
7.35 (2H t) m-phenyl 7.18 (1H t) p-phenyl
7.08 (2H d) o-phenyl 3.89 (1H broad s) Hα
3.06 (2H m) Hε
1.79 (2H m), 1.48 (3H m) and 1.37 (1H m) Hβ, Hγ and Hδ.

EXAMPLE 2

Preparation of $N^\delta$-PhOC-D-ornithine from D-ornithine $N^\delta$-PhOC-D-ornithine was prepared, with an identical yield, according to the same procedure as $N^\omega$-PhOC-lysine of Example 1.

m.p.=197°–199° C. (decomp.)
α=−17.8 (c=1.1/1N HCl)
TLC: Rf (3)=0.54
HPLC: $t_R$=9.69 min.

EXAMPLE 3

Preparation of $N^\gamma$-PhOC-D-diaminobutyric acid from D-diaminobutyric acid $N^\gamma$-PhOC-D-diaminobutyric acid was prepared, with a yield of 65% according to the same procedure as $N^\epsilon$-PhOC-lysine of Example 1.

m.p.=202°–204° C.
TLC: Rf (3)=0.60
HPLC: $t_R$=7.55 min.

EXAMPLE 4
Synthesis of Z-Ser-Tyr-D-Orn(PhOC)

4.03 g (10 mmol) of Z-Ser-Tyr are dissolved in 15 ml of THF and then neutralised with 1.10 ml (10 mmol) of NMM. The activation of the peptide is carried out at −15° C. by addition of 1.3 ml (10 mmol) of i.BuOCOCl. After 3 minutes, the coupling is carried out by addition of a solution, cooled to 0° C., of persilylated $N^\epsilon$-PhOC-D-ornithine, prepared from a suspension of 3.15 g (12.5 mmol) of $N^\delta$-PhOC-D-ornithine in 6.5 ml (50 mmol) of TMSCN which is refluxed until a clear solution is obtained.

After reacting for 5 minutes at low temperature, the temperature is increased to 20° C. and the mixture is allowed to stand for ½ h. The reaction is stopped by addition of 60 ml of EtOAc and 50 ml of a 5% aqueous solution of $KHSO_4$. After removing the aqueous phase, the organic phase is washed with 20 ml of water and then concentrated to dryness. The residue is dissolved in 60 ml of methanol and the crystallisation of the tri-peptide, in the form of an ammonium salt, is induced by addition of concentrated ammonium hydroxide up to pH 8.

Yield: 5.1 g (78%)
Analytical data for a sample released from its salt:
m.p.: 140°–160° C. (decomp.)
α: −23.3 (c=1.06/MeOH)
TLC: Rf (1)=0.76/Rf (2): 0.70
HPLC: $t_R$=23.43 min
NMR ($^1$H) (ref. $CD_3OD$ at 3.31):

| | |
|---|---|
| 7.30 (7 H m) 5 H of Z, 2 H of PhOC | 7.19 (1 H t) p-PhOC |
| 7.08 (4 H m) 2 H of PhOC, 2 H of Tyr | 6.71 (2 H d) 2 H of Tyr |
| 5.10 (2 H q) phenyl$CH_2$O | 4.67 (1 H q) TyrHα |
| 4.41 (1 H q) OrnHα | 4.17 (1 H t) SerHα |
| 3.79 (2 H m) Serβ's | 3.16 (2 H t) Ornδ's |
| 3.10 (1 H q) TyrβA | 2.90 (1 H q) TyrβB |
| 1.89 (1 H m) 1.74 (1 H m) | |
| 1.50 (2 H m) OrnHβ's + OrnHγ's. | |

EXAMPLE 5
Synthesis of Z-Ser-Tyr-D-Cit 2.0 g (3.15 mmol) of Z-Ser-Tyr-D-Orn(PhOC) obtained in Example 4 are added to a mixture of 20 ml of MeOH and 20 ml of 25% $NH_4OH$. The solution obtained is kept at 40° C. for 75 minutes and then evaporated to dryness. The residue is resuspended in a mixture of 10 ml of water and 10 ml of EtOAc. The crystallisation of the tripeptide Z-Ser-Tyr-Cit is induced by acidifying the aqueous phase (pH 3) by means of a concentrated solution of $KHSO_4$. The peptide is collected by filtration and then dried. Yield: 1.45 g (82%). The analytical data for the tripeptide Z-Ser-Tyr-D-Cit produced are:

m.p.: 132°–138° C. (decomp.)
α: −8.10 (c=1.1/DMF)
TLC: Rf (4)=0.17
HPLC: $t_R$=16.44 min
NMR ($^1$H):
Spectrum identical to that for Z-Ser-Tyr-D-Orn-(PhOC) (Example 4), but disappearance of the resonances of the PhOC group and appearance of the resonances of the carbamoyl group:
5.90 (1H t) NH 5.36 (2H s) $NH_2$

EXAMPLE 6
Synthesis of Z-Ser-Tyr-D-Cit(PhEt)

654 mg (1 mmol) of Z-Ser-Tyr-D-Orn(PhOC), crystallised in the form of its ammonium salt, is suspended in a two-phase system composed of 10 ml of 2% $KHSO_4$ and 20 ml of EtOAc. The mixture is stirred at 50° C. for 1 hour. The organic phase is recovered, concentrated to one half, then treated with 1.22 g (10 mmol) of phenylethylamine. The progress of the reaction can be monitored by TLC. As soon as conversion of the tripeptide is complete, the reaction medium is concentrated to dryness and the solid obtained washed twice with 20 ml of MTBE. The tripeptide is thus recovered in the form of the phenylethylamine salt (Z-Ser-Tyr-D-Cit(PhEt)-NHPhEt). In order to obtain the free tripeptide, the salt it dissolved in a minimum amount of methanol and then precipitated in a large volume of a 5% solution of $KHSO_4$. After filtration and washing with water, the tripeptide Z-Ser-Tyr-D-Cit(PhEt) is obtained.

Yield: 630 mg (95%)
m.p.: 160°–169° C. (decomp.)
α: −21.7 (c=1/MeOH)
TLC: Rf (1)=0.65/Rf (2)=0.51
HPLC: $t_R$=23.59 min
NMR ($^1$H) (ref. DMSO-$d_6$ at 2.49 ppm):
9.12 (1H s) OHTyr 8.16 (1H d) NHOrn 7.91 (1h d) NHTyr 7.35 (5H m) H's Z 7.28 (2H m) +7.17 (3H m) H's of Ph.ethylamine
7.21 (1H d) NHSer 6.99 (2H d) Hδ'sTyr 6.60 (2H d) Hε'sTyr
5.84 (1H t) NH ureido-Orn
5.77 (1H t) NH ureido-phenylethylamine
5.01 (2H q) $CH_2$ Z 4.48 (1H m) HαTyr 4.13 (1H m) HαOrn
4.05 (1H m) HαSer 3.48 (2H d) Hβ'sSer
3.19 (2H q) NH$\underline{CH_2}$ phenylethylamine 2.92 (2H q) Hδ'sOrn
2.87 (1H q) HβATyr 2.69 (1H q) HβBTyr
2.64 (2H t) $\underline{CH_2}$Ph. phenylethylamine 1.63 (1H m) HβAOrn
1.50 (1H m) HβBOrn 1.28 (2H m) Hγ'sOrn

EXAMPLE 7
Synthesis of Z-Ser-Tyr-D-Cit(2-methylbutyl)

The synthesis of Example 6 was repeated using 2-methylbutylamine in place of phenylethylamine. Z-Ser-Tyr-D-Cit(2-methylbutyl) was obtained.

TLC: Rf (1)=0.63/Rf (2)=0.52
HPLC: $t_R$=23.07 min
NMR ($^1$H): compared with the starting material (Example 4), the lines for the PhOC group disappeared and the lines for the 2-methylbutylamine residue appeared at 3.03 and 2.90 for the N—$\underline{CH_2}$—; at 1.40 for the N—$CH_2$—CH($CH_3$)—$\underline{CH_2}$—; at 1.12 for the N—$CH_2$—$\underline{CH}$—, at 0.89 for the N—$CH_2$—CH($CH_3$)—$CH_2$—$\underline{CH_3}$ and at 0.87 for the N—$CH_2$—CH($\underline{CH_3}$)—

EXAMPLE 8
Synthesis of Z-Ser-Tyr-D-Cit(tetramethylene)

The synthesis of Example 6 was repeated using pyrrolidine in place of phenylethylamine. Z-Ser-Tyr-D-Cit (tetramethylene) was obtained.

TLC: Rf (1)=0.35/Rf (2)=0.21
HPLC: $t_R$=19.18 min
NMR ($^1$H): the lines due to the pyrrolidine residue are situated at 3.30 (4H) and at 1.87 (4H)

EXAMPLE 9
Synthesis of Z-Ser-Tyr-D-Orn(PhOC) from Z-Ser-Tyr-D-Orn a) Synthesis of Z-Ser-Tyr-D-Orn(Pht)

The tripeptide Z-Ser-Tyr-D-Orn(Pht) is first prepared by reaction of Z-Ser-Tyr with δ-Pht-D-ornithine according to a procedure similar to that of Example 4. The desired tripeptide is obtained in the form of an ammonium salt, with a yield of 85%.

Analytical data:
HPLC: $t_R$=24.06 min

NMR ($^1$H) (in DMSO-$d_6$):

| | | |
|---|---|---|
| 7.80 (4 H, m) H'sPht | 7.31 (5 H, m) H's Z | 6.96 (2 H, d) HδTyr |
| 6.60 (2 H, d) HεTyr | 4.96 (2 H, q) CH$_2$-Z | 4.41 (1 H m) HαTyr |
| 4.15 (1 H, m) HαOrn | 3.99 (1 H, m) HαSer | 3.53 (2 H, m) HδOrn |
| 3.44 (2 H, d) HβSer | 2.83 (1 H dd) HβATyr | 2.67 (1 H dd) HβBTyr |
| 1.65 (1 H m) + | | |
| 1.52 (3 H m) Hβ + | | |
| HγOrn | | | b) Preparation of Z-Ser-Tyr-D-Orn

The side group of the ornithine residue is deprotected by hydrazinolysis: 28 g of Z-Ser-Tyr-D-Orn(Pht) are suspended in 1.3 L of MeOH. After addition of 10 ml of NH$_2$NH$_2$.H$_2$O, the mixture is heated to boiling temperature. After 2 hours, the reaction product begins to crystallise. One hour later, the heating is stopped and the mixture is cooled to room temperature. The precipitate is collected by filtration. After washing with water and with cold methanol, the cake is dried so as to give 90% of pure Z-Ser-Tyr-D-Orn.

HPLC : $t_R$=15.37 min

NMR($^1$H) (in CD$_3$OD):

7.34 (5H m) H-arom. Z 7.08 (2H d) HδTyr 6.73 (2H m) HεTyr 5.09 (1H d) and 4.98 (1H d) CH$_2$—Z 4.59 (1H m) HαTyr 4.45 (1H m) HαOrn 4.13 (1H m) HαSer 3.68 (2H m) HβSer 3.13 (1H dd) HβATyr 2.90 (3H m) HβBTyr+HδOrn 1.94 (1H m), 1.77 (1H m) and 1.63 (2H m) Hβ+HγOrn c) Synthesis of Z-Ser-Tyr-D-Orn(PhOC)

The PhOC group is introduced into the side chain of the ornithine residue in the following manner:

5.17 g (10 mmol) of Z-Ser-Tyr-D-Orn are dissolved in 50 ml of a 1:1 THF:H$_2$O mixture by volume. Then the pH is adjusted to 7.5 by addition of TEA. 3.54 g (15 mmol) of PhOC-OSu are then introduced into the reactor. The conversion is complete after allowing the mixture to stand for a period of 2 h 30 min. The THF is removed under vacuum, then 100 ml of EtOAc and, with stirring, 25 ml of a 10% aqueous solution of KHSO$_4$ are added. The decanted organic phase is washed with 50 ml of water, and then concentrated to dryness. The residue is taken up in 50 ml of MeOH and the pH is adjusted to 8 by means of concentrated ammonium hydroxide. The tripeptide Z-Ser-Tyr-D-Orn(PhOC) crystallises in the form of an ammonium salt. It is identical to the produce synthesised via the direct route described in Example 4.

EXAMPLE 10
Synthesis of NH$_2$-CO-Ala-Phe a) Synthesis of PhOC-Ala 20 mmol of alanine are treated under reflux with 30 mmol of TMSCN until complete solubilisation is obtained. After dilution with 30 ml of dichloromethane, the mixture is cooled to −15° C. 20 mmol of phenyl chloroformate are then slowly added. After 10 minutes, the solution is concentrated to dryness, the residue is taken up in 40 ml of dichloromethane and washed with 50 ml of a 5% aqueous solution of citric acid and then with 50 ml of water. The organic phase is concentrated, taken up in 40 ml of hot sulphuric ether, and then diluted with hexane until the mixture becomes torbid. After overnight storage in a refrigerator, the crystals formed are filtered, washed and dried to give 3.6 g of PhOC-Ala (yield=86%).

m.p.: 119°–124° C.

α: −45.6 (c=1/MeOH)

HPLC: $t_R$=13.45 min

NMR($^1$H): (In CDCl$_3$; for some protons, two forms appear, Major=M minor=m):

| | | |
|---|---|---|
| 7.36 (2 H t) PhOC meta | 7.21 (1 H t) PhOC para | 7.14 (2 H d) PhOc ortho |
| 6.51 (d) NH-m and 5.62 (d) NH-M | | 4.49 (1 H quint) Hα |
| 1.60 (d) CH$_3$-m | | 1.55 (d) CH$_3$-M | b) Synthesis of PhOC-Ala-Phe 2.1 g (10 mmol) of PhOC-Ala, dissolved in 10 ml of dichloromethane are neutralised with 1.1 ml (10 mmol) of NMM. The solution, cooled to −10° C., is treated with 1.3 ml (10 mmol) of i.BuOCOCl. After activating for 4 minutes at −10° C., the solution of persilylated phenylalanine is added and after allowing to stand for 1 hour at room temperature, the dipeptide formed is desilylated by addition of 0.2 ml of water. Then the mixture is washed with 100 ml of a 3% aqueous solution of KHSO$_4$. The PhOC-Ala-Phe crystallises from the two-phase system. After overnight storage in a refrigerator, it is recovered by filtration. Yield: 3.1 g (86%)

m.p.: 143°–144° C.

α: −19.5 (c=1/MeOH)

HPLC: $t_R$=22.63 min

NMR ($^1$H) (in CDCl$_3$)

| | |
|---|---|
| 7.3 to 7.1 (10 H m) H aromat. PhOC + Phe | 6.74 (1 H d) NH Phe |
| 6.12 (1 H d) NH Ala  4.77 (1 H q) HotPhe | 4.23 (1 H quint) HαAla |
| 3.20 (1 H dd) HβAPhe  3.06 (1 H dd) HβBPhe | | c) conversion to NH$_2$—CO-Ala-Phe 30 mg of PhOC-Ala-Phe are dissolved in 0.5 ml of a 1:1 mixture by volume of concentrated ammonium hydroxide (25%) and MeOH. After 3 hours, HPLC analysis indicates a complete and selective conversion (by-products <2%). The reaction medium is diluted with THF until the mixture becomes turbid. After overnight storage in a refrigerator, a theoretical quantity of NH$_2$-CO-Ala-Phe is recovered in the form of an ammonium salt by filtration.

α: 33.1 (c=0,4/H$_2$O)

HPLC: $t_R$=10.14 min

NMR ($^1$H) in DMSO-$d_6$:

| | | |
|---|---|---|
| 7.48 (1 H d) NHPhe | 7.13 (5 H m) H arom.Phe | 6.33 (1 H d) NHAla |
| 5,62 (2 H s) NH$_2$-CO | 4.08 (1 H q) HαPhe | 3.99 (1 H quint) HαAla |
| 3.07 (1 H dd) HβAPhe | 2.89 (1 H dd) HβBPhe | 1.10 (3 H d) CH$_3$Ala. |

EXAMPLE 11
Synthesis of PhOC-Phe-Val

To 2.04 g (5 mmol) of persilylated Phe-Val (TMS-Phe-Val-OTMS) is added a solution of 20 ml of EtOAc containing 1.17 g (5 mmol) of PhOC-OSu. After 2 minutes, 15 ml of water are added. The two-phase system is stirred for 15 minutes and then the aqueous phase is removed. The organic phase is extracted twice with 10 ml of water. The residue of the organic phase after evaporation consists of 1.6 g of PhOC-Phe-Val, contaminated with trace amounts of Phe-Val. By taking up this residue in a two-phase water/MTBE system, the free dipeptide is extracted into the aqueous phase and the residue of the organic phase is PhOC-Phe-Val with a peptide purity greater than 95%.

TLC: Rf(2)=0.86

HPLC: $t_R$=25.2 min

NMR ($^1$H) (ref. CD$_3$OD at 3.30 ppm)

| | |
|---|---|
| 7.30 (7 H m) 5H Phe, 2H m-PhOC | 7.17 (1 H t) p-PhOC |
| 6.98 (2 H d) o-PhOC | 4.56 (1 H t) Hα Phe |
| 4.39 (1 H d) Hα Val | 3.22 (1 H dd) Hβ-1 Phe |
| 2.92 (1 H dd) Hβ-2 Phe | 2.20 (1 H m) Hβ Val |
| 1.00 (6 H m) 2 × CH$_3$ Val | |

What is claimed is:

1. A method for producing a stereochemically preserved peptide containing at least one N-carbamoyl functional group comprising reacting an intermediate peptide containing one or more aryloxycarbonyl groups consisting of a group of general formula

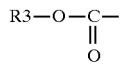

attached to the nitrogen atom of an amino functional group and in which R3 is selected from the group consisting of phenyl, naphthyl, tolyl, xylyl, mesitylyl, ethylphenyl, diethylphenyl, propylphenyl and isopropylphenyl with a compound of general formula R1R2NH in which R1 and R2 represent, independently of each other, hydrogen atoms, alkyl, cycloalkyl or aralkyl radicals, containing at most 12 carbon atoms, or in which R1 and R2 together form an alicyclic radical containing 3 to 6 carbon atoms, to produce said peptide.

2. The method according to claim 1, wherein R3 is a phenyl or p-tolyl group.

3. The method according to claim 1, wherein the intermediate peptide bears an aryloxycarbonyl group on one or more ω-amino functional groups.

4. The method according to claim 1, wherein the intermediate peptide is synthesised starting with the N-aryloxycarbonyl derivative of an amino acid.

5. The method according to claim 4, wherein the intermediate peptide is synthesised starting with the N$^\omega$-aryloxycarbonyl derivative of a diamino acid.

6. The method according to claim 1, wherein the intermediate peptide is synthesised starting with a precursor peptide, by introducing the aryloxycarbonyl group onto the amino functional group(s) to be carbamoylated inside the peptide chain.

7. The method according to claim 1, wherein R3 is phenyl.

8. The method according to claim 1, wherein the compound R1R2NH is used in a quantity 2 to 100 times greater than a stoichiometric quantity.

9. A method for producing a peptide containing at least one N-carbamoyl functional group, comprising the steps of:

a) synthesizing an intermediate peptide containing at least one aryloxycarbonyl group consisting of a group of general formula

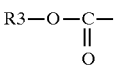

attached to a nitrogen atom of an amino functional group and in which R3 is selected from the group consisting of phenyl, naphthyl, tolyl, xylyl, mesitylyl, ethylphenyl, diethylphenyl, propylphenyl and isopropylphenyl, by coupling of amino acids, at least one of said amino acids bearing said aryloxycarbonyl group attached to a nitrogen atom of an amino functional group, wherein, after incorporation into a peptide fragment of said amino acid bearing said aryloxycarbonyl group, the intermediate peptide synthesis is continued by coupling said peptide fragment with amino acids in a conventional manner, the aryloxycarbonyl group acting as a stable blocking group of the amino functional group to which it is attached during the synthesis of said intermediate peptide; and b) reacting said intermediate peptide with a compound of general formula R1R2NH in which R1 and R2 represent, independently of each other, hydrogen atoms, alkyl, cycloalkyl or aralkyl radicals, containing at most 12 carbon atoms, or in which R1 and R2 together form an alicyclic radical containing 3 to 6 carbon atoms, to produce said peptide containing at least one N-carbamoyl functional group, the aryloxycarbonyl group acting as a specific intermediate for the desired N-carbamoyl functional group.

10. The method according to claim 9, wherein R3 is a phenyl or p-tolyl group.

11. The method according to claim 9, wherein R3 is phenyl.

12. The method according to claim 9, wherein the compound R1R2NH is used in a quantity 2 to 100 times greater than a stoichiometric quantity.

13. The method according to claim 9, wherein the intermediate peptide is synthesized starting with the N$^\omega$-aryloxycarbonyl derivative of an α, ω diamino acid.

14. The method according to claim 9 wherein the peptides produced are selected from the group consisting of peptides containing L, D, or DL norcitrulline, citrulline or homocitrulline residues from corresponding L, D, or DL 2,4-diaminobutyric acid, ornithine, and lysine respective precursor amino acids.

* * * * *

UNITED STATES PATENT AND TRADEMARK OFFICE
CERTIFICATE OF CORRECTION

PATENT NO. : 5,770,692
DATED : June 23, 1998
INVENTOR(S) : Marc Anteunis et al.

It is certified that error appears in the above-identified patent and that said Letters Patent is hereby corrected as shown below:

On the title page, please insert :

-- [73] Assignee:   SOLVAY (Société Anonyme), Brussels, Belgium. -- ; and

Attorney, Agent or Firm—Spencer & Frank --.

Signed and Sealed this

Sixth Day of July, 1999

Attest:

Q. TODD DICKINSON

Attesting Officer

Acting Commissioner of Patents and Trademarks